US00PP30859P2

(12) United States Plant Patent
Kunieda

(10) Patent No.: US PP30,859 P2
(45) Date of Patent: Sep. 3, 2019

(54) ***ROSA L.* VARIETY NAMED '80101WABARA'**

(50) Latin Name: ***Rosa* L.**
Varietal Denomination: 80101WABARA

(71) Applicant: Rose Universe Co., Ltd., Shiga (JP)

(72) Inventor: Keiji Kunieda, Shiga (JP)

(73) Assignee: ROSE UNIVERSE CO., LTD., Shiga (JP)

( * ) Notice: Subject to any disclaimer, the term of this patent is extended or adjusted under 35 U.S.C. 154(b) by 0 days.

(21) Appl. No.: 15/932,567

(22) Filed: Mar. 15, 2018

(30) Foreign Application Priority Data

Jan. 26, 2018 (JP) ..... PBR PVP 32807

(51) Int. Cl.
*A01H 5/02* (2018.01)
*A01H 6/74* (2018.01)

(52) U.S. Cl.
USPC ..... Plt./108

(58) Field of Classification Search
USPC ..... Plt./108
See application file for complete search history.

*Primary Examiner* — Annette H Para
(74) *Attorney, Agent, or Firm* — Kilpatrick Townsend & Stockton

(57) ABSTRACT

Described herein is a new and distinct rose variety named '80101WABARA'.

3 Drawing Sheets

Genus and species: The rose variety of this invention is botanically identified as *Rosa* L.

Variety denomination: The variety denomination is '80101WABARA'.

CROSS-REFERENCES TO RELATED APPLICATIONS

This application claims priority to Japanese Plant Variety Protection Application No. 32807, filed Jan. 26, 2018.

BACKGROUND OF THE INVENTION

The present invention is a new and distinct variety of a *Rosa* L. rose plant obtained from a cross between maternal variety 'Kaorikazari' and an unnamed paternal variety of unknown parentage owned by the breeder. The cross was performed by hand pollination in May 2014 and seeds were planted in January 2015. '80101WABARA' was selected from the varieties that flowered in September 2017. Stable characteristics were confirmed following selection.

BRIEF SUMMARY OF THE INVENTION

'80101WABARA' is reproduced by grafting. '80101WABARA' can be distinguished from a similar variety, 'Yuzen', by: (1) a larger number of petals (70 petals compared to 58 for 'Yuzen'); (2) color grouping (reddish compared to peach for 'Yuzen'); (3) petal shape (ellipitic center part, obcordate outside compared to obovate for 'Yuzen'); (4) main color of the inner side of the petal (RHS N79C compared to RHS 67B for 'Yuzen'); and (5) petal secondary color (RHS N79A compared to absent for 'Yuzen'). '80101WABARA' is also distinguished from comparison variety 'Keiji1002' by the main color of the inner side of the petal (RHS N79C compared to RHS N57C for 'Keiji1002'); and flower fragrance (strong compared to medium for 'Keiji1002').

'80101WABARA' is distinguished from the female parent by color, flower size, and fragrance. The female parent flower color is RHS 44C and the flower is larger in size than the flower of '80101WABARA'. The female parent also has a fruit incense fragrance, whereas '80101WABARA' does not.

'80101WABARA' is distinguished from the male parent by branch length and thickness. The male parent has a branch length of 45 cm and a branch thickness of about 0.3 cm.

The variety '80101WABARA' has been asexually reproduced at 507-2, Kanegamoricho, Moriyama-shi, Shiga, 524-0045 Japan. It is maintained at Shiga-ken Moryama-shi, 1465 Sugie-cho, Japan and is maintained by soil cultivation. The variety is primarily used as a potted plant and for cut flowers. Planting in Japan is from mid-October to late December. Grafting is from late September to early October. The plant will flower annually when grown in a greenhouse.

BRIEF DESCRIPTION OF THE PHOTOGRAPHS

The accompanying photographs illustrate the appearance of the new *Rosa* L. variety. The colors in the photographs are depicted as nearly true as is reasonably possible to obtain in colored reproductions of this type. Colors as shown in the photographs may differ slightly from the color values cited in the detailed botanical description.

Figure 1:
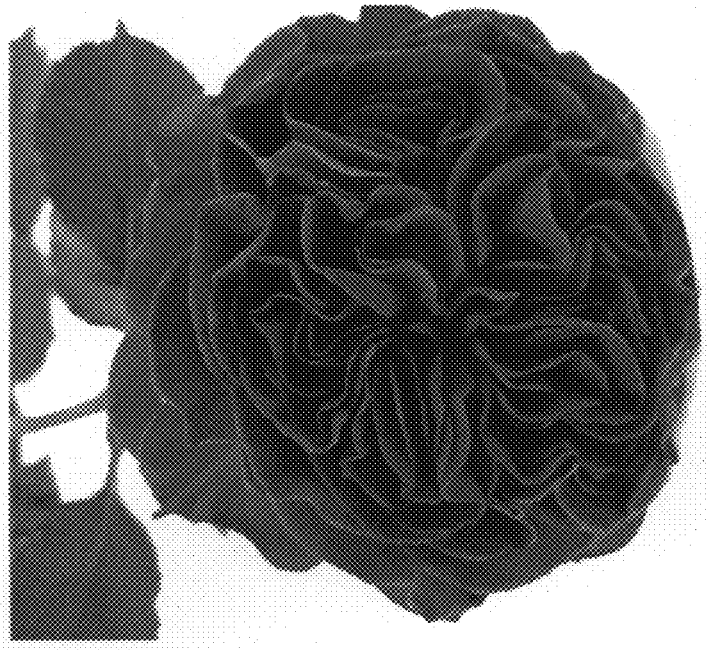
Figure 2:
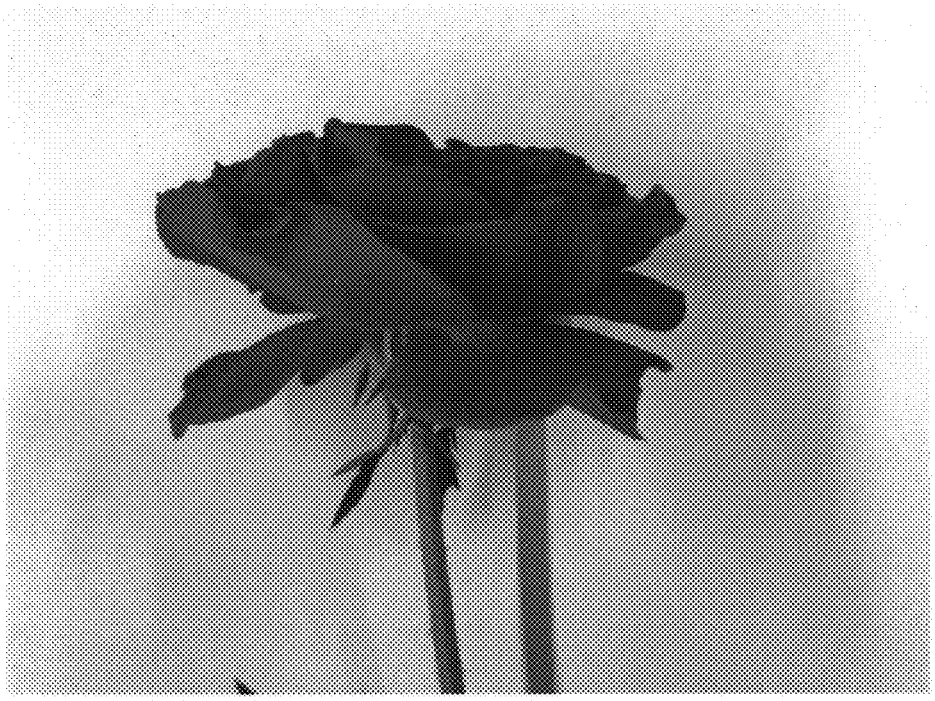
Figure 3:
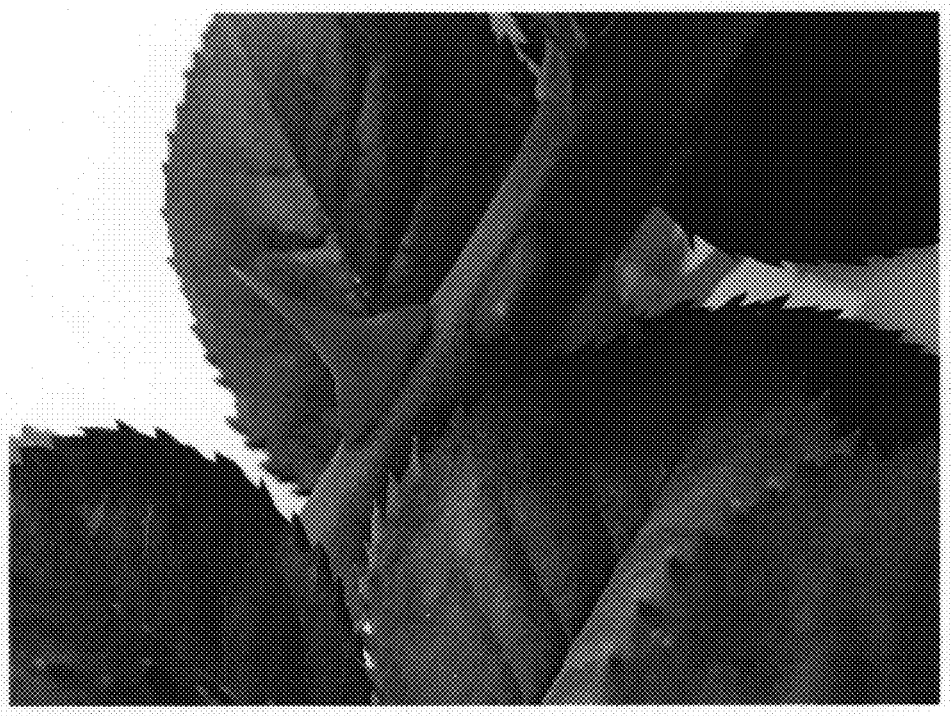
Figure 4:
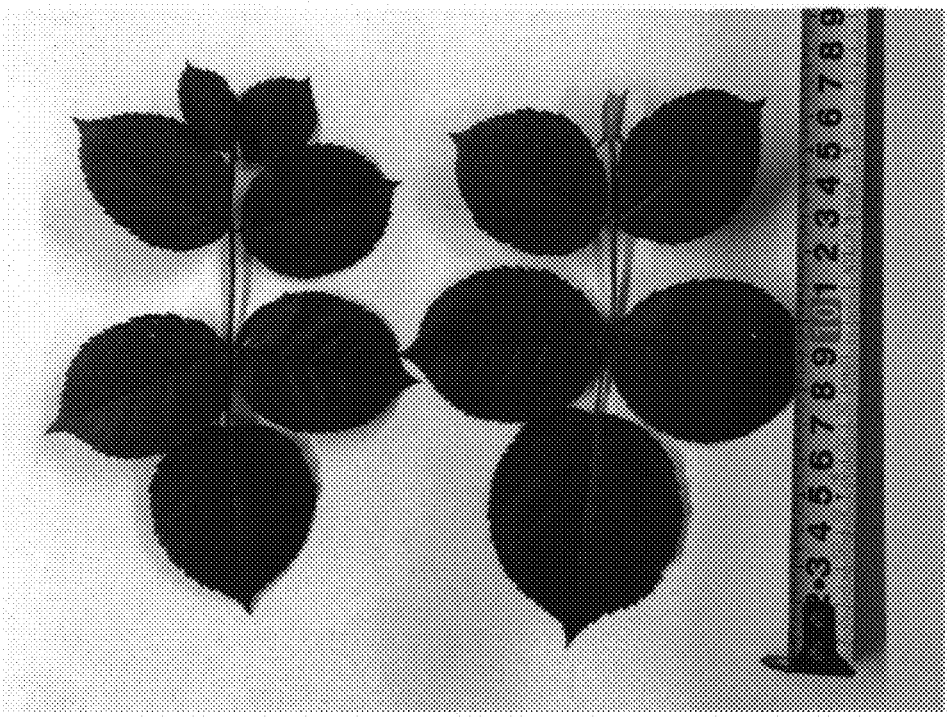
Figure 5:
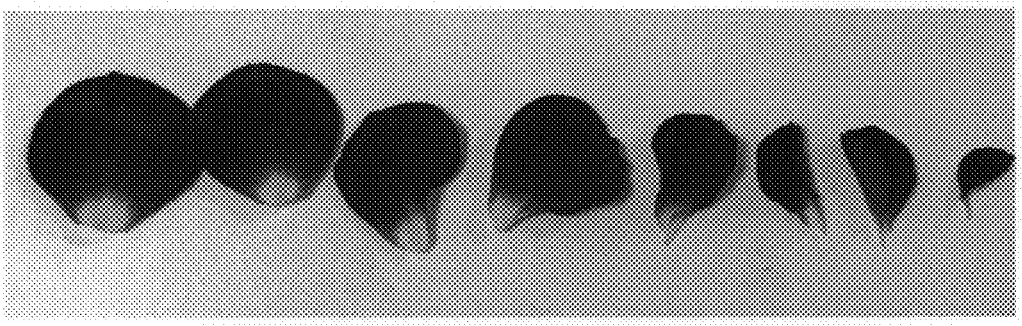
Figure 6:
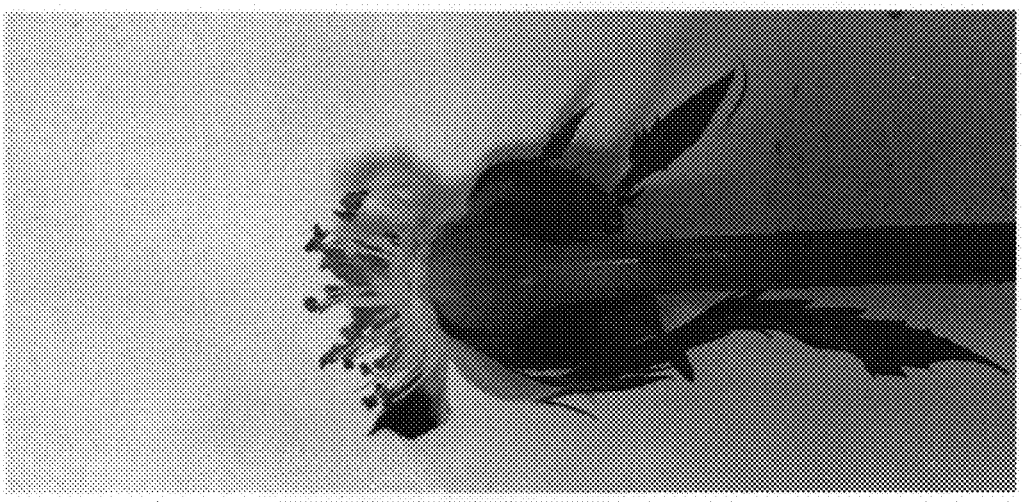

FIG. 1 shows a close-up front view of a flower.
FIG. 2 shows a close-up side view of a flower.
FIG. 3 shows the prickles on a branch.
FIG. 4 shows leaves with leaflets.
FIG. 5 shows individual petals.
FIG. 6 shows reproductive organs of a flower.

DETAILED BOTANICAL DESCRIPTION

The following is a detailed description of '80101WABARA' with color descriptions based on The Royal Horticultural Society (R.H.S.) Colour Chart for those colors referred to by R.H.S. designation.

CHARACTERISTICS OF VARIETY

Plant:

*Growth type*.—Shrub.
*Growth habit*.—Semi-upright.
*Height*.—96 cm.
*Young shoot, anthocyanin coloration*.—Present.
*Stem size*.—About 0.4 cm.
*Stem, number of prickles* (*excluding hair-like prickles*).—Few.
*Prickle size*.—About 1 cm.
*Prickles*.—Predominant color: Reddish, RHS 199B.
*Bark color*.—RHS 138A.

Leaf:

*Size*.—14.2 cm.
*Width of leaf*.—About 4.5 cm.
*Intensity of green color*.—Dark, RHS N138B.
*Anthocyanin coloration*.—Present.
*Glossiness of upper side*.—Weakly glossy.
*Leaflet color*.—RHS N138B.
*Leaflet, undulation of margin*.—Very weak.
*Leaflet, terminal, shape of blade*.—Circular.
*Leaflet, terminal, shape of base of blade*.—Rounded.
*Leaflet, terminal, shape of apex of blade*.—Acuminate.
*Leaflet, terminal leaflet size*.—About 5 cm.
*Terminal leaflet color* (*upper surface*).—RHS N138B.
*Terminal leaflet color* (*lower surface*).—RHS N138B.

Flowers:

*Flowering shoot, flowering laterals*.—Present.
*Flowering shoot, number of flowering laterals*.—1.
*Flowering shoot*.—Number of flowers: 1.
*Flowering shoot*.—Number of flowers per lateral: 1.
*Flower type*.—Double.
*Number of petals*.—70.
*Flower diameter*.—8.5 cm.
*Flower color group*.—Reddish.
*Density of petals* (*for double flowered variety, loose or dense*).—Dense.
*Flower diameter*.—8.5 cm.
*Flower shape*.—Round.
*Profile of upper part of flower*.—Flattened convex.
*Profile of lower part of flower*.—Flattened convex.
*Fragrance*.—Strong.
*Sepal, extensions*.—Very strong.
*Reflexing of petals one-by-one*.—Absent.
*Petal shape*.—Fan-shaped.
*Petal incisions*.—Very weak.
*Reflexing of petal margin*.—Medium (center part is strong).
*Petal undulation*.—Weak (center part is medium).
*Petal length*.—3 cm.
*Petal width*.—4.7 cm.
*Number of colors on inner side of petal*.—Two.
*Main color on inner side of petal*.—RHS N79C.
*Secondary color of petal*.—RHS N79A.
*Distribution of secondary color on inner side of petal*.—Stripes.
*Basal spot on the inner side of petal*.—Present.
*Size of basal spot on inner side*.—Small.
*Color of basal spot on inner side*.—Medium yellow.
*Main color on the outer side of petal*.—RHS 59C.
*Distribution of color of petals*.—Middle zone (middle part) 70-80%; spot at the base 20-30%.
*Outer stamen, predominant color of filament*.—Light Yellow.

What is claimed is:

1. A new and distinct variety of a *Rosa* L. rose plant having the characteristics substantially as described and illustrated herein.

* * * * *